US011033239B2

(12) United States Patent
Cheenepalli et al.

(10) Patent No.: US 11,033,239 B2
(45) Date of Patent: Jun. 15, 2021

(54) ALERT SYSTEM FOR AUDITORY QUEUES

(71) Applicant: INTERNATIONAL BUSINESS MACHINES CORPORATION, Armonk, NY (US)

(72) Inventors: Bhargav Cheenepalli, Charlotte, NC (US); Kristin E. McNeil, Charlotte, NC (US); Stephen Douglas Bowman, Monroe, NC (US); David Blake Werts, Charlotte, NC (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

(21) Appl. No.: 16/580,440

(22) Filed: Sep. 24, 2019

(65) Prior Publication Data

US 2021/0085261 A1    Mar. 25, 2021

(51) Int. Cl.
*A61B 5/00*   (2006.01)
*G06F 9/54*   (2006.01)
*G06N 20/00*  (2019.01)
*G16H 10/60*  (2018.01)
*G06F 40/169* (2020.01)
*G06F 40/205* (2020.01)
*G11B 3/00*   (2006.01)

(52) U.S. Cl.
CPC .............. *A61B 5/74* (2013.01); *G06F 9/542* (2013.01); *G06F 40/169* (2020.01); *G06F 40/205* (2020.01); *G06N 20/00* (2019.01); *G11B 3/00* (2013.01); *G16H 10/60* (2018.01)

(58) Field of Classification Search
CPC ....... A61B 5/74; G06F 40/205; G06F 40/169; G06F 9/542; G06N 20/00; G16H 10/60
See application file for complete search history.

(56) References Cited

U.S. PATENT DOCUMENTS

| | | | |
|---|---|---|---|
| 6,064,963 A | 5/2000 | Gainsboro | |
| 8,612,261 B1* | 12/2013 | Swanson | G16H 10/60 705/3 |
| 9,867,023 B2 | 1/2018 | Rauner | |
| 10,318,928 B1* | 6/2019 | Kestone | G08B 21/02 |
| 2002/0019749 A1* | 2/2002 | Becker | G16H 70/20 705/2 |
| 2004/0006628 A1* | 1/2004 | Shepard | H04L 69/329 709/228 |
| 2008/0172232 A1 | 7/2008 | Gurley | |
| 2008/0231429 A1* | 9/2008 | Leonard | G06F 19/324 340/146.2 |
| 2013/0191149 A1 | 7/2013 | Kolberg et al. | |
| 2014/0207686 A1 | 7/2014 | Experton | |
| 2015/0294089 A1 | 10/2015 | Nichols | |
| 2017/0116373 A1* | 4/2017 | Ginsburg | G16H 40/20 |
| 2018/0336318 A1 | 11/2018 | Bhatt et al. | |

* cited by examiner

*Primary Examiner* — Ryan W Sherwin
(74) *Attorney, Agent, or Firm* — F. Chau & Associates, LLC (57) ABSTRACT

Systems and methods for generating alerts based on potential health conflicts are described. The described systems and methods may provide for identifying unstructured text from a physical environment, performing natural language processing on the unstructured text to produce annotated text, comparing the annotated text to patient medical information to find a potential conflict, and generating an alert based on the potential conflict.

20 Claims, 5 Drawing Sheets

ALERT SYSTEM FOR AUDITORY QUEUES

BACKGROUND

The following relates generally to an alert system, and more specifically to an alert system based on patient information.

Medical patients have a wide variety of different needs other than those directly related to medical treatment. For example, a patient may have allergies that warrant special consideration. However, doctors and nurses process many patients in a given day. This results in the doctors and nurses moving quickly between patients. In some cases, medical treatment facilities create standards for performing tasks to increase efficiency. For example, a hospital may have standard medications, standard ointments, standard food, etc. However, a patient's special considerations (such as allergies, medication conflicts, medications conflicting with other medications, etc.) may be overlooked when performing standardized tasks. In some cases, a patient may be able to alert medical staff to an issue, but in other cases patients may be unable to do so. For example, a patient may be under anesthesia, unable to speak, or have a lack of knowledge about the conflict. As a result, mistakes might occur that impact patient health outcomes.

In some cases, mistakes may occur even if a patient alerts medical staff to an allergy or other medical consideration. For example, a doctor or a nurse may forget about the allergy while performing a procedure. The information may be stored in a medical record, but such data can easily be overlooked or misread. Therefore, there is a need in the art for systems and methods that help medical staff avoid making mistakes that result from overlooking the special considerations of their patients.

SUMMARY

A method, apparatus, non-transitory computer readable medium, and system for generating alerts based on potential health conflicts are described. The method, apparatus, non-transitory computer readable medium, and system may provide for identifying unstructured text from a physical environment, performing natural language processing on the unstructured text to produce annotated text, comparing the annotated text to patient medical information to find a potential conflict, and generating an alert based on the potential conflict.

DETAILED DESCRIPTION

The present disclosure describes systems and methods for generating alerts based on potential health risks identified based on analyzing unstructured text. Embodiments of the disclosure convert audio signals (such as voices) occurring around a patient to text and perform natural language processing (NLP) on this text in real-time.

The described systems may also perform NLP (either machine learning or rules based) on the patient's medical record to identify allergies or other special considerations. If an allergy or special consideration is found in the record, this information is stored. The real-time voice NLP analysis may then compare the set of special considerations to words or phrases that may indicate a conflict (i.e., mention of the allergy or a product that contains an allergen). If a conflict is detected, an alert mechanism may be triggered.

Embodiments of the present disclosure may enable medical professionals to avoid errors. This may result in decreases costs, improved patient service, improved patient outcomes, and reduced malpractice liability.

Figure 1:
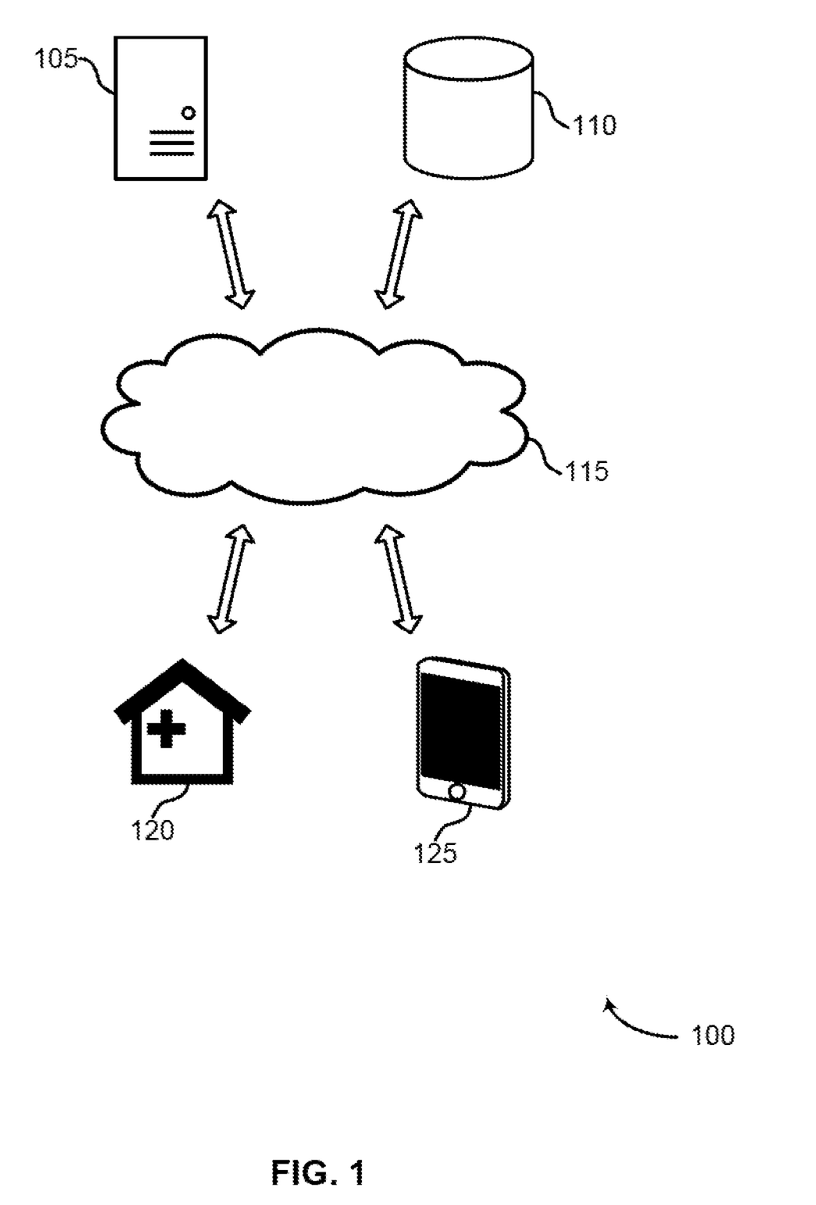
FIG. 1 shows an example of a system in accordance with aspects of the present disclosure.

FIG. 1 shows an example of an alert system 100 in accordance with aspects of the present disclosure. Alert system 100 may include a server 105, database 110, network 115, environment 120, and device 120. Server 105 and database 110 may communicate with each other via network 115. Network 115 may then communicate with environment 120, which may then communicate with device 125.

According to embodiments of the present disclosure, unstructured text may be gathered from the environment 120 (i.e., via an audio or video sensor in a medical operating room). This unstructured text may be analyzed by the server 105. Patient medical records may be stored in the database 110, and analyzed by the server 105 to identify potential health risk factors. These health risk factors are compared to the unstructured text that has been analyzed (i.e., the text from the environment 120) to determine whether the text indicates a conflict with any health risk factors from the patient's medical record. If a conflict is found, an alert may be generated on the device 125 (i.e., to alert a medical professional of the potential conflict).

In some cases, the input from the environment may include image recognition input in addition to, or as an alternative to the unstructured text. The environment 120 may include a medical environment, or a first responder environment, or any other location where patient medical information may be relevant.

Figure 2:
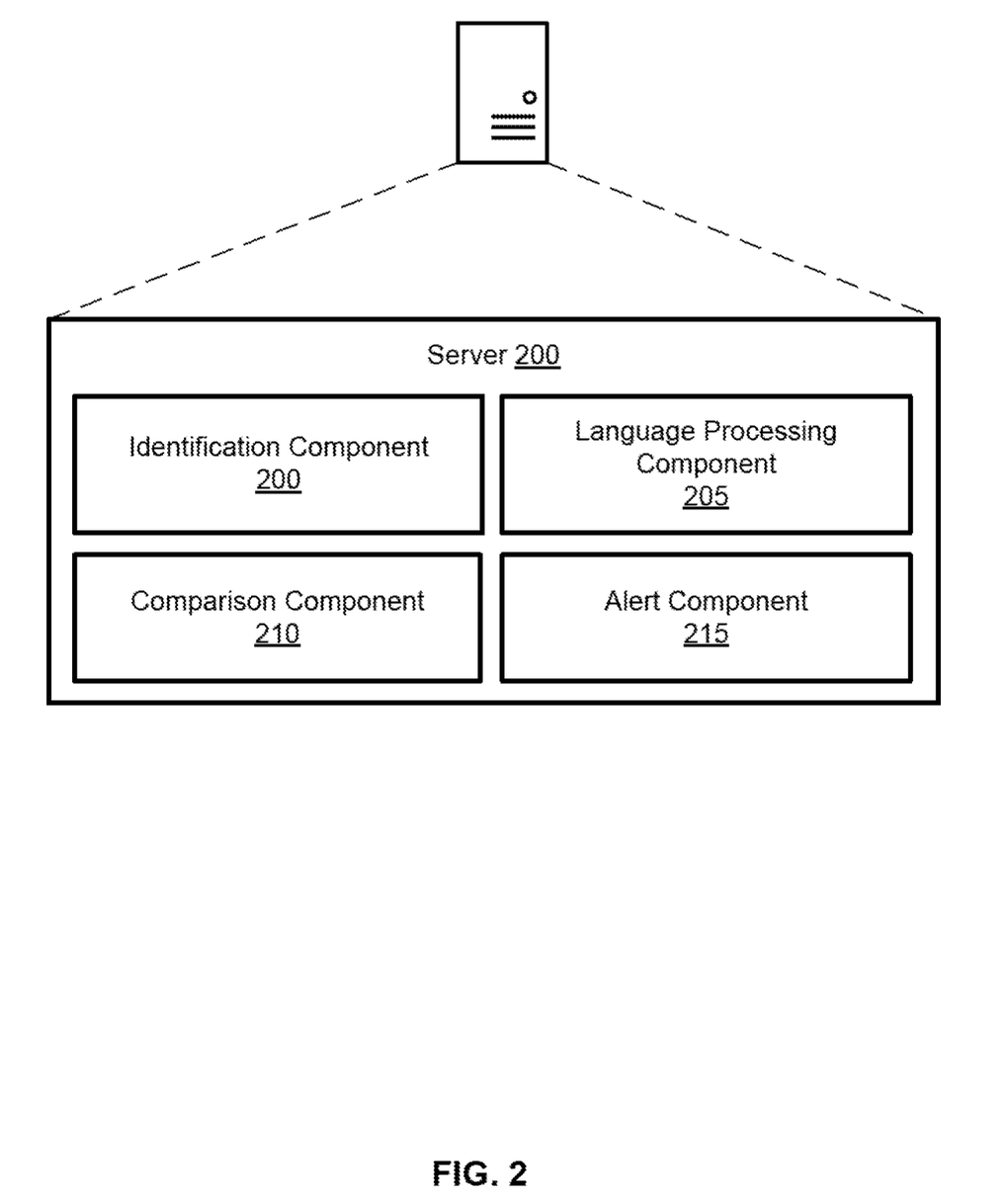
FIG. 2 shows an example of a server in accordance with aspects of the present disclosure.

FIG. 2 shows an example of a server 200 in accordance with aspects of the present disclosure. The example shown includes identification component 200, language processing component 205, comparison component 210, and alert component 215. The server 200 may contain the necessary computing hardware and software to notify medical professionals to previous patient records. Server 200 communicates with network 115 to perform these functions.

A server 200 may provide one or more functions to requesting users linked by way of one or more of the various networks. In some cases, the server 200 may include a single microprocessor board, which may include a microprocessor responsible for controlling all aspects of the server 200. In some cases, a server 200 may use microprocessor and protocols to exchange data with other devices/users on one or more of the networks via hypertext transfer protocol (HTTP), and simple mail transfer protocol (SMTP), although other protocols such as file transfer protocol (FTP), and simple network management protocol (SNMP). In some cases, a server 200 may be configured to send and receive hypertext markup language (HTML) formatted files (e.g., for displaying web pages). A server 200 may be a general-purpose computing device, a personal computer, a laptop computer, a mainframe computer, a supercomputer, or any other suitable processing apparatus.

Identification component 200 identifies unstructured text from a physical environment, receive an audio signal from the physical environment, and convert the audio signal to the unstructured text. Identification component 200 may also receive a video signal from the physical environment and extract the unstructured text from the video signal.

Language processing component 205 performs natural language processing on the unstructured text to produce annotated text and generate metadata based on the unstructured text, where the annotated text includes the metadata. Additionally, language processing component 205 may also apply one or more inference rules to produce additional risk information, where the metadata includes the additional risk information. Language processing component 205 may utilize natural language processing (NLP), which is a branch of artificial intelligence that helps computers understand, interpret and manipulate human language.

Comparison component 210 compares the annotated text to patient medical information to find a potential conflict, receive a patient medical record, and perform natural language processing on the patient medical record to generate a set of risk factors, where the patient medical information includes the set of risk factors. In some examples, the set of risk factors includes allergies, prior medications, diseases, medical history, lab values, movement restrictions, sensitivities, or any combination thereof. Comparison component 210 may also identify a patient located in the physical environment and retrieve the patient medical information based on the identification of the patient. In some examples, the patient is identified based on an electronic identification device, a radio frequency identification device, a schedule, a recognition application, or any combination thereof.

Alert component 215 generates an alert based on the potential conflict. In some examples, the alert includes an audio alert, a visible alert, textual, haptic or any combination thereof. In some examples, the alert includes information regarding the potential conflict.

In some cases the server 200 may utilize an artificial neural network (ANN) for identifying health risk factors (both from the medical records or from the unstructured text from the environment). An ANN may be a hardware or a software component that includes a number of connected nodes (a.k.a., artificial neurons), which may be seen as loosely corresponding to the neurons in a human brain. Each connection, or edge, may transmit a signal from one node to another (like the physical synapses in a brain). When a node receives a signal, it can process the signal and then transmit the processed signal to other connected nodes. In some cases, the signals between nodes comprise real numbers, and the output of each node may be computed by a function of the sum of its inputs. Each node and edge may be associated with one or more node weights that determine how the signal is processed and transmitted. Thus, when unstructured text is provided as an input to the ANN, it may make a prediction about health risk factors that may be indicated by the unstructured text. In some cases, the output of the ANN may be combined with (or based on) a synonym file to produce a set of associated risks.

During the training process, the weights of the ANN may be adjusted to improve the accuracy of the result (i.e., by minimizing a loss function which corresponds in some way to the difference between the current result and the target result). The weight of an edge may increase or decrease the strength of the signal transmitted between nodes. In some cases, nodes may have a threshold below which a signal is not transmitted at all. The nodes may also be aggregated into layers. Different layers may perform different transformations on their inputs. The initial layer may be known as the input layer and the last layer may be known as the output layer. In some cases, signals may traverse certain layers multiple times.

Figure 3:
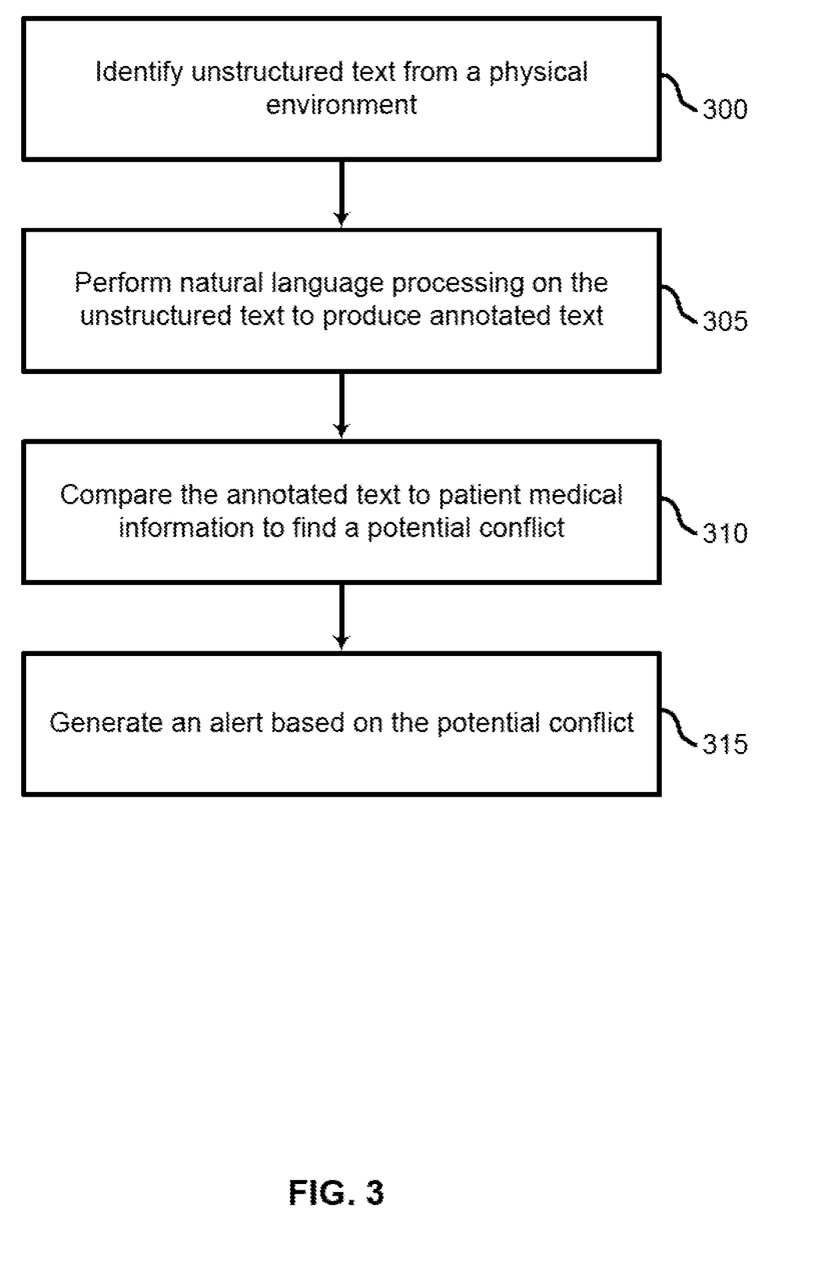
FIG. 3 shows an example of a process for generating alerts based upon patient information in accordance with aspects of the present disclosure.

FIG. 3 shows an example of a process for generating alerts based upon patient information in accordance with aspects of the present disclosure. In some examples, these operations may be performed by a system including a processor executing a set of codes to control functional elements of an apparatus. Additionally or alternatively, the processes may be performed using special-purpose hardware. Generally, these operations may be performed according to the methods and processes described in accordance with aspects of the present disclosure. For example, the operations may be composed of various sub steps, or may be performed in conjunction with other operations described herein.

At step 300, the system identifies unstructured text from a physical environment. In some cases, the operations of this step may refer to, or be performed by, an identification component as described with reference to FIG. 2. For example, the system may receive audio or video signal from the physical environment. The audio or video signal may be converted to text (or, in some cases, semantic information may be identified from an image recognition function).

At step 305, the system performs natural language processing on the unstructured text to produce annotated text. In some cases, the operations of this step may refer to, or be performed by, a language processing component as described with reference to FIG. 2. Unstructured text may be extracted from an audio or video signal. In some examples, metadata based on the unstructured text may also be generated. The metadata may include potential health risk factors, synonyms for different health risk factors, or other data relevant to identifying potential health conflicts.

In at least one embodiment, unstructured information is converted to unstructured text using an automated speech-to-text application. In some cases, the unstructured text may be converted into a form suitable for input into a natural language processing program, such as a machine learning model. In some examples, unstructured information is provided as an input to a machine learning model, and annotated text comprises an output of the machine learning model. The machine learning model may be trained using unstructured text as the training input and a training target comprising known annotations. In some cases, the annotation comprises a prediction of a machine learning model, which may be accompanied by an indication of a confidence level.

In some embodiments, the natural language processing includes applying one or more algorithms to identify and extract the natural language rules such that the unstructured language data is converted into a structured form that can be compared to other health risk data. When the text has been provided, the system may utilize one or more algorithms (which may include machine learning algorithms or other processing rules rules) to extract semantic meaning and collect the health risk data. Thus, the natural language processing may take a first electronic data format as input and output a second electronic data format that includes the annotated text data.

At step 310, the system compares the annotated text to patient medical information to find a potential conflict. In some cases, the operations of this step may refer to, or be performed by, a comparison component as described with reference to FIG. 2. A patient's medical record may be received from a medical records database. In some cases, the records comprise electronic medical records (EMR). Natural language processing is performed on the patient medical record to generate a set of risk factors, and the patient medical information may include the set of risk factors. The set of risk factors may include allergies, prior medications, diseases, medical history, lab values, movement restrictions, sensitivities, or any combination thereof.

In some cases, the system identifies the patient located within the environment (i.e., based on a patient identification bracelet, and radio identifier, a room schedule, or a direct input) and then retrieves the patient's health information based on the identification.

At step 315, the system generates an alert based on the potential conflict. In some cases, the operations of this step may refer to, or be performed by, an alert component as described with reference to FIG. 2. An alert may include an audio alert, a visible alert, textual alerts, haptic alerts or any combination thereof.

Figure 4:
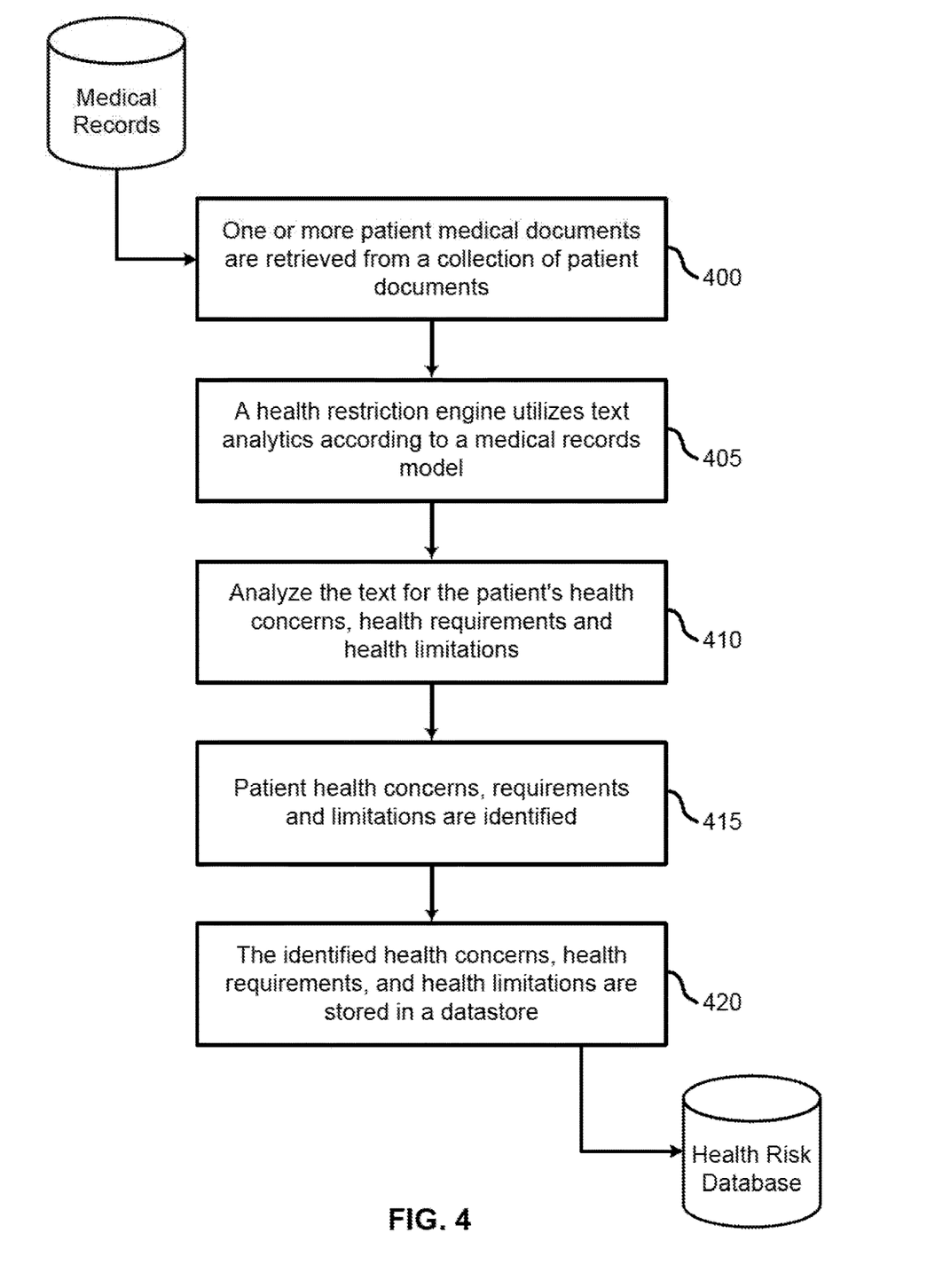
FIG. 4 shows an example of patient medical document retrieval in accordance with aspects of the present disclosure.

FIG. 4 shows an example of patient medical document retrieval in accordance with aspects of the present disclosure. In some examples, these operations may be performed by a system including a processor executing a set of codes to control functional elements of an apparatus. Additionally or alternatively, the processes may be performed using special-purpose hardware. Generally, these operations may be performed according to the methods and processes described in accordance with aspects of the present disclosure. For example, the operations may be composed of various sub steps, or may be performed in conjunction with other operations described herein.

At step 400, one or more patient medical documents may be retrieved from a collection of patient documents. In some cases, the operations of this step may refer to, or be performed by, an identification component as described with reference to FIG. 2.

At step 405, a health restriction engine may utilize text analytics according to a medical records model. In some cases, the health restriction engine may be a part of the language processing component as described with reference to FIG. 2.

At step 410, the system analyzes the text for the patient's health concerns, health requirements and health limitations. In some cases, the operations of this step may refer to, or be performed by, a language processing component as described with reference to FIG. 2.

At step 415, patients health concerns, requirements and limitations may be identified. In some cases, the operations of this step may refer to, or be performed by, a comparison component as described with reference to FIG. 2.

At step 420, the system then identifies health concerns, health requirements, and health limitations are stored in a datastore. In some cases, the operations of this step may refer to, or be performed by, a comparison component as described with reference to FIG. 2.

Figure 5:
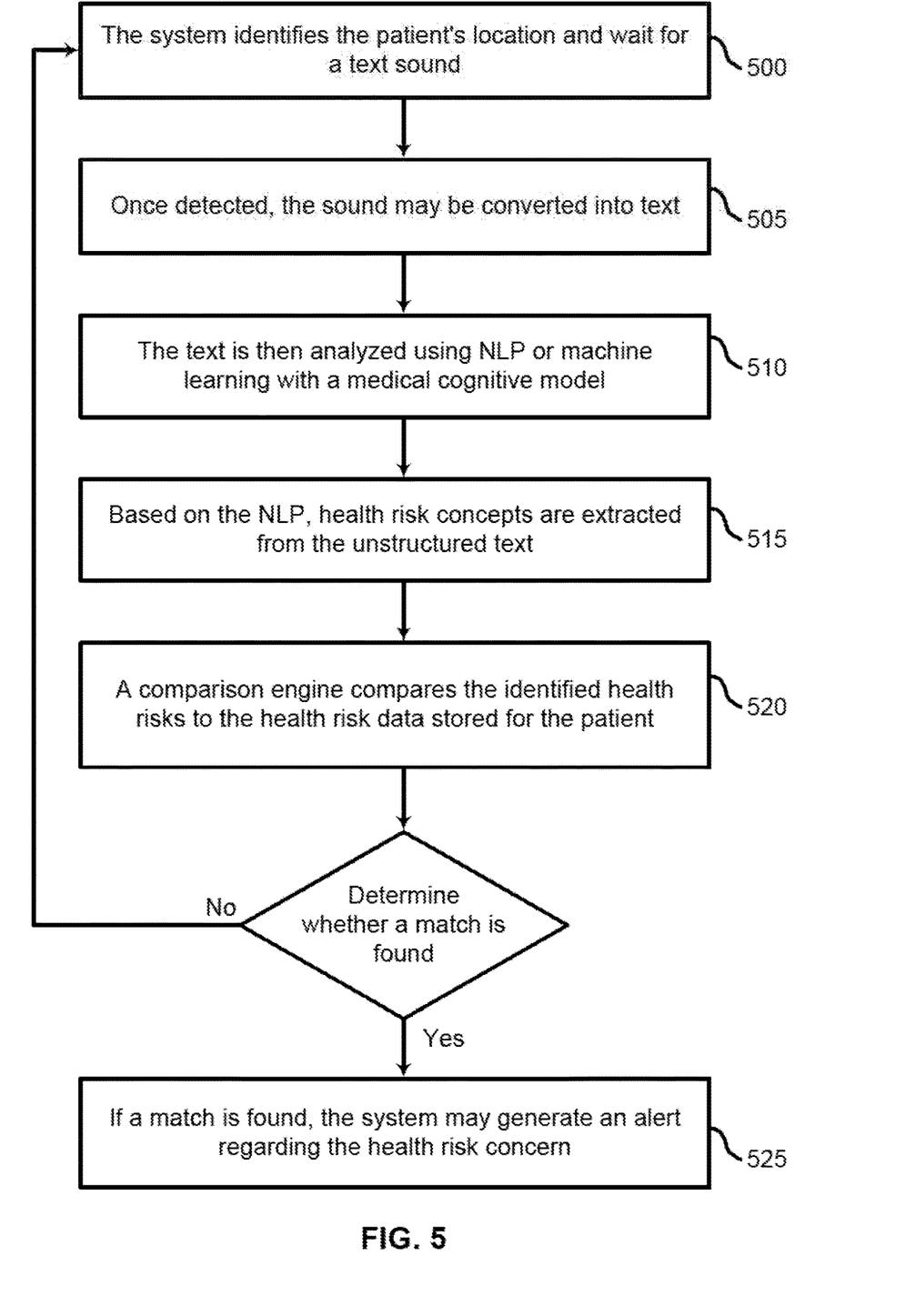
FIG. 5 shows an example of alert generation in accordance with aspects of the present disclosure.

FIG. 5 shows an example of alert generation in accordance with aspects of the present disclosure. In some examples, these operations may be performed by a system including a processor executing a set of codes to control functional elements of an apparatus. Additionally or alternatively, the processes may be performed using special-purpose hardware. Generally, these operations may be performed according to the methods and processes described in accordance with aspects of the present disclosure. For example, the operations may be composed of various sub steps, or may be performed in conjunction with other operations described herein.

At step 500, the system may identify the patient's location and wait for a text sound. In some cases, the operations of this step may refer to, or be performed by, an alert component as described with reference to FIG. 2.

At step 505, once detected, the sound may be converted into text. In some cases, the operations of this step may refer to, or be performed by, an alert component as described with reference to FIG. 2.

At step 510, the text is then analyzed using NLP or machine learning with a medical cognitive model. In some cases, the operations of this step may refer to, or be performed by, an alert component as described with reference to FIG. 2.

At step 515, based on the NLP, health risk concepts are extracted from the unstructured text. In some cases, the operations of this step may refer to, or be performed by, an alert component as described with reference to FIG. 2.

At step 520, the system's comparison engine compares the identified health risks to the health risk data stored for the patient. In some cases, the operations of this step may refer to, or be performed by, an alert component as described with reference to FIG. 2.

If no match is found, the system will revert back to step 500.

At step 525, if a match found, the system may generate an alert regarding the health risk concern. In some cases, the operations of this step may refer to, or be performed by, an alert component as described with reference to FIG. 2.

Accordingly, the present disclosure includes the following embodiments.

A method for generating alerts based on potential health conflicts is described. The method may include identifying unstructured text from a physical environment, performing natural language processing on the unstructured text to produce annotated text, comparing the annotated text to patient medical information to find a potential conflict, and generating an alert based on the potential conflict.

An apparatus for generating alerts based on patient information is described. The apparatus may include a processor, memory in electronic communication with the processor, and instructions stored in the memory. identify unstructured text from a physical environment, perform natural language processing on the unstructured text to produce annotated text, compare the annotated text to patient medical information to find a potential conflict, and generate an alert based on the potential conflict.

A non-transitory computer readable medium storing code for generating alerts based on patient information is described. In some examples, the code comprises instructions executable by a processor to: identify unstructured text from a physical environment, perform natural language processing on the unstructured text to produce annotated text, compare the annotated text to patient medical information to find a potential conflict, and generate an alert based on the potential conflict.

A system for generating alerts based on potential health conflicts is described. The system may include means for identifying unstructured text from a physical environment, means for performing natural language processing on the unstructured text to produce annotated text, means for comparing the annotated text to patient medical information to find a potential conflict, and means for generating an alert based on the potential conflict.

Some examples of the method, apparatus, non-transitory computer readable medium, and system described above may further include receiving an audio signal from the physical environment. Some examples may further include converting the audio signal to the unstructured text.

Some examples of the method, apparatus, non-transitory computer readable medium, and system described above may further include receiving a video signal from the physical environment. Some examples may further include extracting the unstructured text from the video signal.

Some examples of the method, apparatus, non-transitory computer readable medium, and system described above may further include generating metadata based on the unstructured text, wherein the annotated text includes the metadata.

Some examples of the method, apparatus, non-transitory computer readable medium, and system described above may further include applying one or more inference rules to produce additional risk information, wherein the metadata comprises the additional risk information.

Some examples of the method, apparatus, non-transitory computer readable medium, and system described above may further include receiving a patient medical record. Some examples may further include performing natural language processing on the patient medical record to generate a set of risk factors, wherein the patient medical information comprises the set of risk factors.

In some examples, the set of risk factors comprises allergies, prior medications, diseases, medical history, lab values, movement restrictions, sensitivities, or any combination thereof.

Some examples of the method, apparatus, non-transitory computer readable medium, and system described above may further include identifying a patient located in the physical environment. Some examples may further include retrieving the patient medical information based on the identification of the patient.

In some examples, the patient is identified based on an electronic identification device, a radio frequency identification device, a schedule, a recognition application, or any combination thereof.

In some examples, the alert comprises an audio alert, a visible alert, textual, haptic or any combination thereof.

In some examples, the alert comprises information regarding the potential conflict.

The description and drawings described herein represent example configurations and do not represent all the implementations within the scope of the claims. For example, the operations and steps may be rearranged, combined or otherwise modified. Also, structures and devices may be represented in the form of block diagrams to represent the relationship between components and avoid obscuring the described concepts. Similar components or features may have the same name but may have different reference numbers corresponding to different figures.

Some modifications to the disclosure may be readily apparent to those skilled in the art, and the principles defined herein may be applied to other variations without departing from the scope of the disclosure. Thus, the disclosure is not limited to the examples and designs described herein but is to be accorded the broadest scope consistent with the principles and novel features disclosed herein.

The described methods may be implemented or performed by devices that include a general-purpose processor, a digital signal processor (DSP), an application specific integrated circuit (ASIC), a field programmable gate array (FPGA) or other programmable logic device, discrete gate or transistor logic, discrete hardware components, or any combination thereof. A general-purpose processor may be a microprocessor, a conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). Thus, the functions described herein may be implemented in hardware or software and may be executed by a processor, firmware, or any combination thereof. If implemented in software executed by a processor, the functions may be stored in the form of instructions or code on a computer-readable medium.

Computer-readable media includes both non-transitory computer storage media and communication media including any medium that facilitates transfer of code or data. A non-transitory storage medium may be any available medium that can be accessed by a computer. For example, non-transitory computer-readable media can comprise random access memory (RAM), read-only memory (ROM), electrically erasable programmable read-only memory (EEPROM), compact disk (CD) or other optical disk storage, magnetic disk storage, or any other non-transitory medium for carrying or storing data or code.

Also, connecting components may be properly termed computer-readable media. For example, if code or data is transmitted from a website, server, or other remote source using a coaxial cable, fiber optic cable, twisted pair, digital subscriber line (DSL), or wireless technology such as infrared, radio, or microwave signals, then the coaxial cable, fiber optic cable, twisted pair, DSL, or wireless technology are included in the definition of medium. Combinations of media are also included within the scope of computer-readable media.

In this disclosure and the following claims, the word "or" indicates an inclusive list such that, for example, the list of X, Y, or Z means X or Y or Z or XY or XZ or YZ or XYZ. Also the phrase "based on" is not used to represent a closed set of conditions. For example, a step that is described as "based on condition A" may be based on both condition A and condition B. In other words, the phrase "based on" shall be construed to mean "based at least in part on."

What is claimed is:

1. A method for generating health alerts, comprising:
   identifying a location of a patient in a physical environment;
   receiving an audio signal occurring around a patient during a medical procedure based on the identified location of the patient;
   identifying unstructured text from the physical environment based on the received audio signal;
   performing natural language processing on the unstructured text to produce annotated text;
   comparing the annotated text to patient medical information to find a potential conflict; and
   generating an alert based on the potential conflict.

2. The method of claim 1, further comprising:
   converting the received audio signal to the unstructured text.

3. The method of claim 1, further comprising:
   receiving a video signal from the physical environment; and
   extracting additional unstructured text from the video signal.

4. The method of claim 1, further comprising:
generating metadata based on the unstructured text, wherein the annotated text includes the metadata.

5. The method of claim 4, further comprising:
applying one or more inference rules to produce additional risk information, wherein the metadata comprises the additional risk information.

6. The method of claim 1, further comprising:
receiving a patient medical record; and
performing natural language processing on the patient medical record to generate a set of risk factors, wherein the patient medical information comprises the set of risk factors.

7. The method of claim 6, wherein:
the set of risk factors comprises allergies, prior medications, diseases, medical history, lab values, movement restrictions, sensitivities, or any combination thereof.

8. The method of claim 1, further comprising:
identifying the patient located in the physical environment; and
retrieving the patient medical information based on the identification of the patient.

9. The method of claim 8, wherein:
the patient is identified based on an electronic identification device, a radio frequency identification device, a schedule, a recognition application, or any combination thereof.

10. The method of claim 1, wherein:
the alert comprises an audio alert, a visible alert, textual, haptic or any combination thereof.

11. The method of claim 1, wherein:
the alert comprises information regarding the potential conflict.

12. An apparatus for generating alerts based on patient information, comprising: a processor and a memory storing instructions and in electronic communication with the processor, the instructions executable by the processor to:
identify a location of a patient in a physical environment;
receive an audio signal occurring around a patient during a medical procedure based on the identified location of the patient;
identify unstructured information from the physical environment based on the received audio signal;
perform natural language processing on the unstructured information to produce annotated text;
compare the annotated text to patient medical information to find a potential conflict; and
generate an alert based on the potential conflict.

13. The apparatus of claim 12, the processor being further configured to execute the instructions to:
convert the audio signal to the unstructured information.

14. The apparatus of claim 12, the processor being further configured to execute the instructions to:
receive a patient medical record; and
perform natural language processing on the patient medical record to generate a set of risk factors, wherein the patient medical information comprises the set of risk factors.

15. The apparatus of claim 12, the processor being further configured to execute the instructions to:
identify the patient located in the physical environment; and
retrieve the patient medical information based on the identification of the patient.

16. A non-transitory computer readable medium storing code for generating alerts based on patient information, the code comprising instructions executable by a processor to:
identify a location of a patient in a physical environment;
receive an audio signal occurring around a patient during a medical procedure based on the identified location of the patient
identify unstructured information from the physical environment based on the received audio signal;
produce annotated text by processing the unstructured information using a machine learning model, wherein the unstructured information is provided as an input to the machine learning model and at least a portion of the annotated text comprises an output of the machine learning model;
compare the annotated text to patient medical information to find a potential conflict; and
generate an alert based on the potential conflict.

17. The non-transitory computer readable medium of claim 16, the code further comprising instructions executable by the processor to:
convert the audio signal to the unstructured information.

18. The non-transitory computer readable medium of claim 16, the code further comprising instructions executable by the processor to:
apply one or more inference rules to produce additional risk information, wherein the annotated text comprises the additional risk information.

19. The non-transitory computer readable medium of claim 16, the code further comprising instructions executable by the processor to:
receive a patient medical record; and
perform natural language processing on the patient medical record to generate a set of risk factors, wherein the patient medical information comprises the set of risk factors.

20. The non-transitory computer readable medium of claim 16, the code further comprising instructions executable by the processor to:
identify the patient located in the physical environment; and
retrieve the patient medical information based on the identification of the patient.

* * * * *